United States Patent
Guerin-Deremaux et al.

(10) Patent No.: US 9,200,087 B2
(45) Date of Patent: Dec. 1, 2015

(54) BRANCHED SOLUBLE GLUCOSE POLYMERS FOR PERITONEAL DIALYSIS

(75) Inventors: Laetitia Guerin-Deremaux, Nieppe (FR); Carole Petitjean, Marquette Lez Lille (FR); Daniel Wils, Morbecque (FR)

(73) Assignee: ROQUETTE FRERES, Lestrem (FR)

( * ) Notice: Subject to any disclaimer, the term of this patent is extended or adjusted under 35 U.S.C. 154(b) by 518 days.

(21) Appl. No.: 13/575,757

(22) PCT Filed: Feb. 1, 2011

(86) PCT No.: PCT/FR2011/050201
§ 371 (c)(1),
(2), (4) Date: Jul. 27, 2012

(87) PCT Pub. No.: WO2011/095736
PCT Pub. Date: Aug. 11, 2011

(65) Prior Publication Data
US 2012/0295873 A1 Nov. 22, 2012

(30) Foreign Application Priority Data
Feb. 2, 2010 (FR) ..................................... 10 50736

(51) Int. Cl.
| | |
|---|---|
| C08B 30/20 | (2006.01) |
| C08B 30/18 | (2006.01) |
| A61K 31/718 | (2006.01) |
| A61K 45/06 | (2006.01) |
| A61M 1/28 | (2006.01) |
| C08B 30/12 | (2006.01) |
| C08L 3/02 | (2006.01) |
| C12P 19/04 | (2006.01) |
| C12P 19/18 | (2006.01) |

(52) U.S. Cl.
CPC ............... *C08B 30/18* (2013.01); *A61K 31/718* (2013.01); *A61K 45/06* (2013.01); *A61M 1/287* (2013.01); *C08B 30/12* (2013.01); *C08B 30/20* (2013.01); *C08L 3/02* (2013.01); *C12P 19/04* (2013.01); *C12P 19/18* (2013.01)

(58) Field of Classification Search
None
See application file for complete search history.

(56) References Cited

U.S. PATENT DOCUMENTS

| | | | |
|---|---|---|---|
| 3,928,135 | A | 12/1975 | Milner |
| 5,837,060 | A | 11/1998 | Fouache nee Ducroquet et al. |
| 2002/0065410 | A1 | 5/2002 | Antrim |
| 2005/0142167 | A1 | 6/2005 | Backer et al. |
| 2005/0159329 | A1 | 7/2005 | Fuertes et al. |
| 2006/0032400 | A1 | 2/2006 | Henning |
| 2010/0273735 | A1 | 10/2010 | Deremaux et al. |

FOREIGN PATENT DOCUMENTS

| | | |
|---|---|---|
| EP | 0 207 676 A2 | 1/1987 |
| EP | 0 667 356 A1 | 8/1995 |
| EP | 1 369 432 A2 | 12/2003 |
| EP | 1 177 216 B1 | 8/2004 |
| EP | 1 548 033 A2 | 6/2005 |
| EP | 1 720 999 B1 | 11/2006 |
| EP | 1 943 908 A1 | 7/2008 |
| WO | 03/106502 A1 | 12/2003 |
| WO | 2004/022602 A1 | 3/2004 |
| WO | 2007/099212 A1 | 9/2007 |

OTHER PUBLICATIONS

Takata et al., "Application of branching enzyme in starch processing" Biocatalysis and Biotransformation (2010) vol. 28 No. 1 pp. 60-63.*
Takata et al., "Fine structural properties of natural and synthetic glycogens" Carbohydrate Research (2009) vol. 344 pp. 654-659.*
Jayakody et al., "Studies on tuber starches. II. Molecular structure, composition and physicochemical properties of yam (Dioscorea sp.) starches grown in Sri Lanka" Carbohydrae Polymers (2007) vol. 69 pp. 148-163.*
Shimonaga et al., "Variation in Storage a-Polyglucans of Red Algae: Amylose and Semi-Amylopectin Types in Porphyridium and Glycogen Type in Cyanidium" Marine Biotechnology (2007) vol. 9 pp. 192-202.*
Hansen et al., "Gel texture and chain structure of amylomaltase-modified starches compared to gelatin" Food Hydrocolloids (2008) vol. 22 pp. 1551-1566.*
Hanashiro et al., "Gel texture and chain structure of amylomaltase-modified starches compared to gelatin" J. Appl. Glycosci. (2009) vol. 56 pp. 65-70.*
Cho et al., "Structural modification and characterization of rice starch treated by Thermus aquaticus 4-a-glucanotransferase" Food Hydrocolloids (2009) vol. 23 pp. 2403-2409.*
International Search Report, dated Apr. 11, 2011, from corresponding PCT application.

* cited by examiner

*Primary Examiner* — Eric Olson
(74) *Attorney, Agent, or Firm* — Young & Thompson

(57) ABSTRACT

The invention relates to branched soluble glucose polymers made of starch having an amylose content of at least 30 wt %, preferably 35 wt % to 80 wt %, having a glycosidic linkage α-1,6 content of 7% to 10%, preferably 8% to 9%, and a MW of 50,000 to 150,000 daltons, characterized in that the polymers are resistant to pancreatic alpha amylase, expressed according to a test "B" for a reducing sugar content of 25% to 35%, and a MW of released products of 6,000 to 12,000 daltons.

12 Claims, No Drawings

BRANCHED SOLUBLE GLUCOSE POLYMERS FOR PERITONEAL DIALYSIS

The invention relates to branched soluble glucose polymers having an α-1,6 glucosidic linkage content of between 7 and 10%, preferably between 8 and 9%, for a narrow weight-average molecular weight (Mw) distribution of between 50 000 and 150 000 daltons.

These branched soluble glucose polymers also have a certain resistance to α-amylase and a low osmolality, of less than 100 mOsm/kg.

For the purpose of the invention, the expression "certain resistance to α-amylase" is intended to mean the ability that these branched soluble glucose polymers have of being relatively nonglycemic and of prolonging the duration of their osmotic power in a medium containing in particular α-amylase (simulating the hydrolysis of products within the peritoneum), thus allowing their use in particular in peritoneal dialysis applications, for long-lasting treatments.

The invention also relates to soluble branched glucose polymers having an entirely specific branched-chain-length distribution profile.

For the purpose of the invention, the term "branched-chain-length distribution profile" is intended to mean the size distribution, expressed as degree of polymerization (or DP), of the α-1,4 linear glucosidic chains linked to other α-1,4 linear glucosidic chains via α-1,6 branching points.

The invention also relates to compositions comprising such branched soluble glucose polymers that can be used in numerous industrial applications, in particular in the pharmaceutical industries and more particularly in peritoneal dialysis.

Finally, the invention relates to a process for producing said branched soluble glucose polymers and also to a process for purifying said polymers such that they are more particularly intended for the production of peritoneal dialysis solutions.

The glucose polymers conventionally produced industrially are prepared by hydrolysis of natural or hybrid starches and derivatives thereof.

These starch hydrolysates are thus produced by acid hydrolysis or enzymatic hydrolysis of starch from cereals or from tuberous plants. They are in fact a mixture of glucose and glucose polymers, of extremely varied molecular weights.

These starch hydrolysates (dextrins, maltodextrins, etc.) produced industrially (with a certain average degree of polymerization or DP) comprise a broad distribution of saccharides containing both linear structures (α-1,4 glucosidic linkages) and branched structures (α-1,6 glucosidic linkages).

These starch hydrolysates, and in particular the maltodextrins, are generally used as a transporter or bulking agent, as a texturing agent, as a spray-drying support, as a fat substitute, as a film-forming agent, as a freezing regulator, as an anticrystallizing agent, or as a nutrition source.

It is known to those skilled in the art that the saccharide composition of maltodextrins determines both their physical and their biological properties.

Thus, their hygroscopicity, their fermentability, their viscosity, their sweetening nature, their stability, their gelling nature and their osmolality are criteria which are conventionally assessed and chosen according to the various fields in which they are used.

Basic knowledge of the physicochemical behavior of these saccharides thus leads to their being incorporated, for example, into peritoneal dialysis solutions.

Peritoneal dialysis consists in introducing a dialysis solution into the peritoneal cavity by means of a catheter.

After a certain amount of time, an exchange of solutes takes place between the blood and the dialysate.

The use of an appropriate osmotic agent makes it possible to drain excess water from the blood to the dialysate and to thus overcome the kidney deficiency.

The conventional method of peritoneal dialysis in order to remove excess water (ultrafiltration) and solutes from the body consists in injecting into the peritoneal cavity a dialysis solution which is hypertonic with respect to the blood through the addition of glucose as an osmotic agent.

The flow through an ideal semi-permeable membrane is mainly determined by the total number of solute particles (osmolality) present in the solution, independently of their size.

On the other hand, in the case of a biological membrane such as the peritoneal membrane, the flow depends only on the solutes not passing through or sparingly passing through the membrane and is not therefore necessarily linked to the total osmolality of the solution.

In addition, the ability of the solutes to pass through the membrane also depends on the shape of the molecules, on their ionic charge and also on their size.

The choice of an ideal osmotic agent is tricky: said agent must enable an osmotic gradient so as to move the water and the toxic substances from the blood to the dialysis solution through the peritoneum.

It must also be nontoxic and biologically inert, while at the same time being metabolizable by the body, a part thereof being assimilated in the blood.

It must not pass through the peritoneal membrane too rapidly, in such a way as to maintain a long-lasting ultra-filtration gradient and to not allow the accumulation of undesirable nondegradable substances in the blood.

Patent EP 207 676 thus teaches that, for use in continuous and ambulatory peritoneal dialysis, starch hydrolysates forming clear and colorless solutions at 10% in water, having an Mw of from 5000 to 100 000 daltons and a low polydispersity index or PI should be preferred.

This results in compositions which contain predominantly high-molecular-weight glucose polymers of between 5000 and 50 000 daltons, which contain no or very little glucose or oligosaccharides with a DP of less than or equal to 3, and no or very little glucose polymers with an Mw of greater than 100 000 daltons.

Indeed, for this application, low-molecular-weight monomers or polymers which rapidly pass through the peritoneal wall are of no interest for creating a long-lasting osmotic pressure gradient, and, furthermore, polymers of very high molecular weight, greater than 100 000 daltons, and which are devoid of any osmotic power, should be avoided and even prohibited since there is a risk of them retrograding and precipitating in the body.

In its patent EP 667 356, the applicant company has proposed a process for producing, from waxy starch, a starch hydrolysate that is completely soluble in water and has a low polydispersity index, less than 2.8, with an Mw of between 8000 and 22 500 daltons.

This process consists in subjecting a starch milk consisting exclusively of amylopectin to acid hydrolysis, then in further hydrolyzing this acid hydrolysate by means of an enzymatic hydrolysis using bacterial α-amylase, and in chromatographing this hydrolysate on macroporous strong cationic resins in alkali metal or alkaline-earth metal form.

This particular starch hydrolysate, also called icodextrin, has an Mw, determined by light scattering, as will be described hereinafter, of from 21 000 to 22 000 daltons.

The majority of the glucose molecules of the icodextrin are α-1,4 linked linear chains (more than 90%) with a small fraction of α-1,6 branched α-1,4 chains (less than 10%).

Icodextrin has allowed a significant decrease in the daily absorption of glucose previously used as an osmotic agent in dialysis solutions, thus providing a real advantage for the treatment of diabetic and/or obese patients for whom the calorie content is a critical factor.

The peritoneal dialysis solutions containing icodextrin as osmotic agent (in particular sold by Baxter Healthcare Corp. under the brand name Extraneal®) are generally used for long daily exchanges (nocturnal in ambulatory continuous peritoneal dialysis and diurnal in automated peritoneal dialysis).

This icodextrin could, however, be further improved if there was an osmotic agent which generated less blood glucose, and the osmotic power of which lasted longer, leading to a significant simplification of the dialysis treatment procedure.

Indeed, since the dialysate yield would be improved, the frequency at which the dialysis bags would be changed would be lower, which would constitute a definite improvement in the patient's quality of life.

Thus, the ideal carbohydrate in peritoneal dialysis should:
be water-soluble,
have a low viscosity,
not retrograde,
induce low glucose appearance kinetics in the systemic circulation,
be hydrolyzed slowly, but be completely degraded by the body's enzymes at the end of this hydrolysis,
exert a long-lasting osmotic pressure.

Indeed, in relation to the last two points, the outcome of the osmotic agents administered in solution in the peritoneal cavity in patients suffering from kidney failure is determined by their stability in the peritoneal fluid, the degree to which they are absorbed into the systemic circulation and their rate of hydrolysis by amylase.

As it happens, the osmotic agents of the prior art all have the drawback of being rapidly hydrolyzed.

From all the above, the result is that there is therefore a need, that has not been met, to have glucose polymers exhibiting notable properties, in particular in terms of stability and solubility, and which by the same token confer, on the products which contain them, a longer lifetime and controlled digestibility, which makes it possible to use them quite particularly in the peritoneal dialysis field.

It is to the applicant company's credit to have reconciled all these objectives, reputed up until now to be difficult to reconcile, by imagining and developing, at the expense of a great deal of research, novel branched soluble glucose polymers, prepared from starch having an amylose content of at least 30% by weight, preferably between 35 and 80% by weight.

As will be exemplified hereinafter, the applicant company has found that the production of glucose polymers having notable properties, in particular in terms of stability, longer lifetime and controlled digestibility, can be obtained as long as amylose-rich starches are used as starting substrate.

The branched glucose polymers in accordance with the invention constitute a novel family of soluble glucose polymers, in the sense that it is very different than those of the prior art, including other highly branched soluble glucose polymers that the applicant company has already proposed and described in its own prior patent applications.

The applicant company has thus overcome a first technical preconception according to which, as is asserted in the international patent application WO 2004/022602, starch-based products which can be used in peritoneal dialysis must have a degree of α-1,6 branching of preferentially between 11 and 18% and a molecular weight of between 10 000 and 200 000.

The applicant company had also considered that only highly branched soluble polymers (degree of branching greater than 10%) could be used in peritoneal dialysis:

in its patent EP 1 369 432, the polymers were highly branched soluble glucose polymers having an α-1,6 linkage content of greater than 10%, preferably between 12 and 30% and an Mw of from 30 000 to 200 000 daltons;

in its patent application EP 1 548 033, the polymers were highly branched soluble glucose polymers having an α-1,6 linkage content of between 13 and 17% and an Mw of from 90 000 to 150 000 daltons;

in its patent application EP 1 994 061, the polymers were highly branched soluble glucose polymers having an α-1,6 linkage content of between 20 and 30% and an Mw of from 20 000 to 30 000 daltons.

As it happens, the branched soluble glucose polymers in accordance with the invention, prepared from starch having an amylose content of at least 30% by weight, preferably between 35 and 80% by weight, have an α-1,6 glucosidic linkage content of between 7 and 10%, preferably between 8 and 9%, and an Mw of between 50 000 and 150 000 daltons.

These polymers are characterized by their notable resistance to α-amylase, which is determined by means of a test which consists in preparing aqueous solutions of branched polymers in accordance with the invention, which is brought into contact with an amylase of pancreatic origin in order to simulate the hydrolysis of products in the peritoneum.

The applicant company has in the past described, in its patent EP 1 177 216, branched soluble glucose polymers having between 2.5 and 10% of α-1,6 glucosidic linkages and an Mw of between 10 000 and $10^8$ daltons.

Prepared in the majority from standard starch and especially from waxy corn starch, none of these compounds exhibited such notable properties of resistance to pancreatic α-amylase, as will be exemplified hereinafter.

Finally, these polymers have an osmolality, determined according to a test "A", having a value of less than 100 mOsm/kg.

The branched soluble glucose polymers in accordance with the invention have an α-1,6 glucosidic linkage content of between 7 and 10%, preferably between 8 and 9%.

Said content is determined by proton NMR analysis.

The degree of branching is then expressed as a percentage, corresponding to the amount of signal from the proton carried by the C1 of an anhydroglucose unit which links another anhydroglucose unit via an α-1,6 linkage, when a value of 100 has been given to all the signals from the glucosidic protons carried by all the C1s of the glucose residues of said soluble glucose polymers.

Under these conditions, the branched soluble glucose polymers in accordance with the invention have an α-1,6 glucosidic linkage content of between 7 and 10%, preferably between 8 and 9%.

This α-1,6 glucosidic linkage content confers on the branched glucose polymers in accordance with the invention a particular structure, in terms of degree of branching with respect to the starch from which they are derived.

This α-1,6 glucosidic linkage content makes the branched glucose polymers according to the invention difficult to digest, which contributes to being able to use them in all applications where a slowed digestion is desired.

The molecular weights of the branched soluble glucose polymers in accordance with the invention are determined by measuring the weight-average molecular weights (Mw).

This value is obtained by size exclusion chromatography on PSS SUPREMA 100 and PSS 5 SUPREMA 1000 columns mounted in series and coupled to a light scattering detector.

The branched glucose polymers in accordance with the invention then have an Mw value of between 50 000 and 150 000 daltons.

The polymers in accordance with the invention are characterized by their notable resistance to α-amylase, said resistance being determined according to a test developed by the applicant company.

This test, termed test "B", makes it possible to evaluate the resistance of the polymers to amylase hydrolysis, which is in particular an essential criterion in the choice of an osmotic agent for a dialysis solution.

According to the test "B", the operating conditions for the amylase digestion are the following:
- accurately weigh out 0.6 g of test product,
- add 150 ml of Na maleate buffer, pH 7, at 0.1 mol/l,
- stir until the product has dissolved,
- place the flask in a thermostated water bath at 37° C. for 15 minutes, so that the temperature of the solution is 37° C.,
- take a sample of 1.5 ml at time 0 minute (sample SI),
- add 0.15 g of porcine pancreatin having an activity equivalent to 8 USP (α-amylase of animal origin),
- incubate at 37° C. in the thermostated bath with stirring (THP 15 Variomag stirrer at three-quarters of its stirring power) for 300 minutes,
- take samples of 1.5 ml at times: 15, 30, 45, 60, 90, 120, 180, 240, 300 minutes,
- stop the enzymatic reaction by placing the samples in a dry bath at 100° C., for 10 minutes,
- assay the reducing sugars on the samples in order to study the rate of hydrolysis,
- determine the average molar masses of the amylase hydrolysis products thus released.

The method used for assaying the reducing sugars is the Somogyi-Nelson method, which consists in:
- introducing 200 microliters of sample into a stoppered tube, and adding to said sample 200 microliters of working solution (sodium tartrate and copper sulfate reagents),
- bringing to boiling and adding, after cooling, arsenomolybdate reagent, and then water.

The solution obtained is deposited on a microplate, and then the absorbance is read on a microplate reader at a wavelength of 520 nanometers.

The reference value for determining the reducing sugars according to the test "B" is that measured at 300 minutes.

With regard to the method used for determining the average molar masses of the amylase hydrolysis products thus released, it is an HPSEC chromatography method on Shodex OH pak-SB802-SB803-SB805 columns.

The elution solvent is a solution of 0.1 M sodium nitrate+ 0.02% sodium azide. The flow rate is 0.5 ml/min. The columns are maintained at a temperature of 30° C.

A refractometer is used as detection module, and the columns are calibrated with pullulans of known molar mass.

The reference value for determining the average molar masses according to the test "B" is also that measured at 300 minutes.

The branched soluble glucose polymers of the invention then exhibit a resistance to pancreatic alpha-amylase expressed according to the test "B" via:
- a reducing sugar content of between 25 and 35%, and
- an Mw of the released products of between 6000 and 12 000 daltons.

A first subfamily of branched soluble glucose polymers in accordance with the invention exhibits a resistance to pancreatic alpha-amylase expressed according to the test "B" via:
- a reducing sugar content of greater than or equal to 25% and less than 30%,
- an Mw of the released products of greater than or equal to 9500 and less than 12 000 daltons.

A second subfamily of branched soluble glucose polymers in accordance with the invention exhibits a resistance to pancreatic alpha-amylase expressed according to the test "B" via:
- a reducing sugar content of greater than or equal to 30% and less than 35%,
- an Mw of the released products of greater than or equal to 6000 daltons and less than 9500 daltons.

The branched soluble glucose polymers in accordance with the invention also have particular osmolality values.

The osmolality of a solution is defined as the amount of moles of a substance dissolved per kg of water.

The osmolality of the branched soluble glucose polymers in accordance with the invention is measured according to the same test "A" as that described in patent application EP 1 369 432, consisting in determining the osmolality of a solution containing 100 g, dry, of branched glucose polymers according to the invention placed in 1 kg of water.

The osmolality of this solution is measured on a Mark osmometer from Fiske™ Associates, according to the constructor's specifications, and gives an osmolality value of less than 100 mOsm/kg.

This value complies with what one must expect of a compound intended for peritoneal dialysis (values that are too high mean strong bonding of said compounds with water, which impairs their passage through the semipermeable membrane of the peritoneum).

Osmolality values that are notably less than those of blood (300 mOsm/kg) are recommended.

The first subfamily of branched soluble glucose polymers in accordance with the invention as presented hereinabove then has a notably low osmolality, of between 10 and 20 mOsm/kg.

The second subfamily of branched soluble glucose polymers in accordance with the invention as presented hereinabove has, for its part, an osmolality of between 50 and 100 mOsm/kg.

Finally, the branched soluble glucose polymers in accordance with the invention are characterized by their chain-length distribution profile.

The determination of the length of the branched chains of the branched soluble glucose polymers in accordance with the invention is carried out in two steps.

A first step consists in debranching said products (specific hydrolysis of the α-1,6 linkage) using a bacterial isoamylase, followed by a second step of identifying the degree of polymerization of the oligosaccharides released, by size exclusion chromatography (HPSEC) in comparison with pullulans of known size.

This technique consists in weighing out 50 mg of product to be analyzed and adding thereto 3.75 ml of water. After stirring of this mixture, 0.5 ml of dimethyl sulfoxide (DMSO) is added and the mixture is brought to boiling with stirring for 30 minutes.

The temperature is then reduced to 45° C. and 0.25 ml of 1M sodium acetate buffer solution (brought to pH 3.5 beforehand with acetic acid) is added.

An isoamylase extracted from *Pseudomonas amyloderasoma*, sold by the company Hayashibara (in a proportion of 59 000 U/mg), is then added and left to act at 45° C. for 20 minutes.

This addition is repeated 20 times, and then the reaction is stopped by boiling for 3 minutes.

The solution is then demineralized using Amberlite 200 and Amberlite IRA-67 resins sold respectively by the companies Fluka and Sigma.

The solution is then filtered through a nylon filter with a pore size of 0.45 µm, before being injected onto an HPSEC column.

The HPSEC chromatography is parameterized in the following way (on a PWXL oligo column sold by TSK and on SB802+803+804+805 columns sold by Shodex):
- injection volume: 200 l
- flow rate: 0.5 ml/min
- column temperature: 40° C.
- eluent: 0.2 M sodium nitrate+0.02% Na azide
- elution time: 180 min.

The size of the oligosaccharides released is determined by means of their elution time compared with the elution time of pullulans of known size.

The branched glucose polymers in accordance with the invention then have a branched-chain-length distribution profile characterized by:
- 25 to 80% of DP<10,
- 2 to 10% of DP>30,
- with an average DP of between 4 and 12.

The first family of branched glucose polymers in accordance with the invention as presented hereinabove has a branched-chain-length distribution profile characterized by:
- 25 to 40% of DP<10,
- 5 to 10% of DP>30,
- with an average DP of between 10 and 12.

The second family of branched glucose polymers in accordance with the invention as presented hereinabove has a branched-chain-length distribution profile characterized by:
- 65 to 80% of DP<10,
- 2 to 5% of DP>30,
- with an average DP of between 4 and 6.

In comparison, icodextrin has a branched-chain-length distribution profile characterized by:
- 22% of DP<10,
- 16% of DP>30,
- with an average DP of 13.

The branched glucose polymers in accordance with the invention are thus characterized in that they have, in particular compared with icodextrin, a distinct chain-length distribution (a significantly higher content of DP<10 for a lower content of DP>30).

This branched-chain-length distribution thus confers on the branched glucose polymers in accordance with the invention an entirely particular structure, made of branched short chains.

The invention also relates to a peritoneal dialysis solution, characterized in that it comprises, as osmotic agent, at least one branched soluble glucose polymer, obtained by enzymatic treatment of starch, having
- an α-1,6 glucosidic linkage content of between 7 and 10%, preferably between 8 and 9%,
- a weight-average molecular weight (Mw), determined by light scattering, of between 50 000 and 150 000 daltons.

The peritoneal dialysis solution according to the invention can also comprise physiologically acceptable electrolytes, such as in particular sodium, potassium, calcium, magnesium or chlorine, so as to avoid the loss by transfer of electrolytes from the serum to the peritoneum.

When the solution is obtained by dissolving the branched polymers according to the invention in water, it should be clear and colorless.

It is free of endotoxins, of peptidoglycans and of β-glucans, and also of contaminants originating from the raw material or from the enzymatic preparations used to produce it.

To this effect, the highly branched polymers used in said solution will preferably have undergone purification so as to remove any coloration or any unwanted contaminant such as proteins, bacteria, bacterial toxins, fibers, traces of metals, etc, as will be illustrated hereinafter.

The dialysis solution according to the invention may also comprise buffering agents (lactate, acetate, gluconate in particular) and other additives, such as amino acids, insulin, polyols such as, for example, sorbitol, erythritol, mannitol, maltitol or xylitol, or hydrogenated starch hydrolysates.

The addition of polyols to the composition, and preferably of apyrogenic polyols free of the impurities described above (endotoxins and other residues of bacterial origin in particular), makes it possible to increase the osmolality of the solution more advantageously than with glucose or maltose, owing to their greater osmotic power and because they are not reducing.

Finally, it is also possible to complete the dialysis solution containing the highly branched soluble glucose polymers of the invention with glucose, maltose and/or glucose polymers.

Amino acid-based peritoneal dialysis solutions are of definite value in the prevention of accelerated aging of the peritoneum associated with glucose and its derivatives, even though their cost and the risk of a tricky regulation of acidosis limits the exclusive and continuous prescription thereof.

It is therefore possible to envision making up a mixture of various molecules in the same peritoneal dialysis solution: glucose, highly branched soluble glucose polymers in accordance with the invention, and amino acids.

It is therefore preferred to sterilize these various constituents separately (use of compartmentalized bags), in order to avoid in particular the generation of glucose degradation products (GDPs) or products resulting from the binding of glucose to said amino acids (or AGEs) responsible for harmful effects on the stability of the peritoneal membrane.

The dialysis solution according to the invention is, moreover, advantageous compared with the products of the prior art, since the osmotic agent that it contains makes it possible to exert a long-lasting osmotic pressure and induces slow glucose appearance kinetics, while at the same time being stable to retrogradation, thus meeting the principal criteria defined above.

In order to prepare the branched soluble glucose polymers in accordance with the invention, a process comprising the succession of the following steps can be carried out:

1) bursting and solubilization of a milk of starch having an amylose content of at least 30% by weight, preferably between 35 and 80% by weight, and a dry matter content of between 5 and 25%, 2) continuous addition of a glycogen-branching enzyme extracted from thermophilic microorganisms, having an activity of between 25 000 U/ml and 60 000 U/ml at a dose of between 800 and 2500 U/g, dry, of starch, at a temperature of between 60° C. and 80° C. for a period of from 12 to 18 hours, 3) optionally, treatment with a starch-liquefying enzyme of α-amylase type having an activity of between 100 and 150 KNU/ml at a temperature of 95° C., a pH of between 5 and 8, for 30 to 60 minutes, preferably for 45 minutes, 4) purification of the resulting branched soluble glucose polymers by means of:
- at least one step of treatment with activated carbon and/or with granular black carbon,
- at least one sterilizing filtration step, and
- optionally, at least one heat treatment step, 5) recovery of the resulting purified branched soluble glucose polymers.

The process for modifying the amylose-rich starch with branching enzymes consists, firstly, in cooking the starch so that it is in the partially or totally gelatinized form.

This first step of the process in accordance with the invention corresponds to the bursting and solubilization of an amylose-rich starch milk, this solubilization of the starch being intended to allow the treatment with the branching enzymes.

For the purpose of the invention, the term "amylose-rich starch" is intended to mean a starch having an amylose content of at least 30% by weight, preferably between 35 and 80% by weight.

In one embodiment of the process in accordance with the invention, a pea starch milk with a dry matter content of between 5 and 25% is prepared, and is heated, by any technique known moreover to those skilled in the art, at a temperature greater than or equal to the gelatinization temperature of the starch, preferentially between 100 and 200° C., even more preferentially between 140 and 160° C., at a pressure of from 4 to 5 bar for 3 to 5 minutes.

For the purpose of the invention, the term "branching enzymes" is intended to mean the branching enzymes chosen from the group consisting of glycogen-branching enzymes.

More particularly, these branching enzymes are extracted from thermophilic organisms and/or microorganisms.

After this step of total or partial solubilization of the starch, the branching enzymes are continuously introduced into the reaction medium under conditions which limit the formation of intermolecular complexes.

More particularly, the conditions for introducing the branching enzymes into the reaction medium are regulated in terms of time and temperature so as to limit the formation of insoluble materials resulting from retrogradation of the starch and of structured amylose-lipid associations.

The starch paste thus partially or totally gelatinized is therefore cooled so as to bring it to the optimum temperature of the selected branching enzyme.

For example, if the thermostable glycogen-branching enzyme extracted from thermophilic microorganisms of the Bacillus genus (B. stearothermophilus, B. megaterium, etc.) is selected, it is necessary to bring the starch paste to the optimum operating temperature of the enzyme, i.e. between 60 and 80° C.

It will be advantageously chosen to rapidly cool the partially or totally gelatinized starch paste from its initial temperature of between 140 and 160° C. down to a temperature from 60 to 80° C., over a period of less than 15 minutes, allowing immediate addition of the branching enzyme in order to avoid retrogradation of the starch or the formation of structured amylose-lipid associations.

The pH of the solution is then adjusted so as to bring it to a value in accordance with the operating mode of said enzyme.

As will be exemplified hereinafter, after the step of rapid lowering of the temperature of the reaction medium to the optimum operating temperature of the branching enzyme, it is chosen to use said branching enzyme at an activity of between 25 000 U/ml and 60 000 U/ml at a dose of between 800 and 2500 U/g, dry, of pea starch, at a temperature of between 60° C. and 80° C. for a period of from 12 to 18 hours.

At the end of the reaction, the enzyme can finally be heat-deactivated at a temperature of from 90° C. to 95° C.

The branched soluble glucose polymers are thus obtained in an aqueous solution.

The optional third step of the process in accordance with the invention consists in bringing a starch-liquefying enzyme to act, such as an α-amylase.

The reaction conditions (temperature and pH) are the following: from 0.10 to 0.30 ml of α-amylase, for example of the Termamyl® 120 L type from Novozymes having an activity of between 100 and 150 KNU/ml at a temperature of 95° C., a pH of between 5 and 8, for 30 to 60 minutes, preferably for 45 minutes.

The α-amylase is then deactivated by lowering the pH to 3.5, for example using 10% HCl.

At the end of this treatment, the branched soluble glucose polymers in accordance with the invention are obtained in an aqueous solution, as a mixture with their enzymatic degradation products.

Contrary to the teachings of the abovementioned patent applications, in particular EP 1 369 432 and EP 1 548 033, a fractionation using a technique chosen, for example, from the group of membrane separations and chromatographies, so as to recover the high-molecular-weight fractions and to eliminate the low-molecular-weight fractions, is not necessarily carried out here.

Thus, the direct product of the treatment using the branching enzyme alone, and the direct product of the treatment using the branching enzyme and then the α-amylase, constitute the two families of branched soluble glucose polymers previously described:
the first family corresponding to the glucose polymers in accordance with the invention obtained by only the treatment with the branching enzyme;
the second family corresponding to the glucose polymers in accordance with the invention obtained by the joint treatment with the branching enzyme and with the α-amylase.

The fractionation of the products of the second family as described hereinabove, using a technique chosen, for example, from the group of membrane separations and chromatographies, would therefore result in a third family of branched soluble glucose polymers in accordance with the invention.

The fourth step of the process in accordance with the invention consists in purifying the resulting branched soluble glucose polymers by means of:
at least one step of treatment with activated carbon and/or with granular black carbon,
at least one sterilizing filtration step, and
optionally, at least one heat treatment step.

The applicant company, by combining these steps of treatment with activated carbon and/or granular black carbon, of filtration, or even of heat treatment, in a particular arrangement, thus notably succeeds in ensuring a "virtual absence" of contamination, in particular of endotoxins, of β-glucans and of peptidoglycans.

The safe nature of such a process thus makes it possible to limit the bacterial controls, at the end of said process, to the single test for detecting peptidoglycans (for example the high-sensitivity test developed and validated by the applicant company—which will be described hereinafter), and to the conventional test for detecting endotoxins (LAL test=test for detecting bacterial endotoxins, which are major components of Gram-negative bacteria).

For the purpose of the invention, the term "virtual absence" is intended to mean a quantification at thresholds well below what is described in the pharmacopeia tests, i.e.:
for endotoxins (and β-glucans) via the LAL test (gel-clot endpoint method) using reagents produced by Charles River-Endosafe (LAL lysate of sensitivity 0.015 E.U/ml ref. OR15015 and CSE endotoxins 500 ng or 10 ng per bottle ref. E110 or E120): 0.6 EU/g;

for peptidoglycans (and β-glucans) via a high-sensitivity test developed by the applicant company: <8 ng/g of glucose polymers (thus, well below the reference threshold described in patent EP 1 720 999 for peptidoglycans).

The expression "high-sensitivity test developed and validated by the applicant company" is intended to mean a test developed and validated by the applicant company by adapting the SLP-HS single set kit ref. 293-58301 produced and sold by the company Wako Pure Chemical Industries Ltd.

This test consists in adding the "SLP-HS" (Silkworm larvae plasma-high sensitivity) reagent, said reagent being prepared from the silkworm larvae plasma, capable of:
  reacting with the peptidoglycans and β-glucans contained in a solution of glucose polymer prepared at 5% in water (special water for the LAL test, for example),
  inducing a serine-protease cascade reaction, and
  detecting and/or quantifying said peptidoglycans and βglucans by means of a Toxinometer tube reader manufactured and sold by the company Wako Pure Chemical Industries Ltd at very low thresholds, i.e.:
    a limit of detection (LD) at a threshold of approximately 0.05 ng/ml (i.e. 1 ng/g of glucose polymer) and
    a limit of quantification (LQ) at a threshold of approximately 0.15 ng/ml (3 ng/g of glucose polymer)
  (LD and LQ determined in the glucose polymer product tested).

More specifically, the SLP-HP test consists in:
preparing the test glucose polymer in solution at 5% in water of appropriate quality (special water for LAL test for example),
producing a calibration range of peptidoglycans in water over the application range of from 0.04 to 2.5 ng/ml (target values) with the peptidoglycans standard (extracted from *Staphylococcus aureus*) of the SLP-HS single set kit for establishing a straight calibration line (logarithmic-scale linear regression Ta=f(PG content)),
introducing 100 µl of the test solution prepared into the HS-SLP tube after reconstitution by adding 100 µl of the diluent (supplied in the abovementioned kit),
introducing the SLP-HS tube into the incubation well of the Toxinometer tube reader (Wako Pure Chemical Ltd) thermostated at 30° C. and parameterized according to the conditions recommended by the manufacturer.

The PG content of the test solution is calculated by means of the straight calibration line established.

The result is expressed in ng/ml of 5% solution tested and then in ng/g of glucose polymer.

It is notable that, in the end, the amounts of these peptidoglycans/β-glucans in the glucose polymer obtained by means of the process in accordance with the invention are guaranteed to be well below 8 ng/g of glucose polymer.

In the process for purifying the branched soluble glucose polymers intended for peritoneal dialysis, as has been described above, the first step of this purification consists in using activated carbon and/or granular black carbon in a particular configuration.

The applicant company recommends implementing this means in at least one of the following three variations:
  in a first variation of the process in accordance with the invention: in the case of the use of granular black carbon, this configuration is based on operation in the countercurrent mode.

The residence time in the column is approximately three hours. The percolation is carried out at a rate of about 2 m/h at a temperature of about 80° C. in order to avoid bacterial contamination.

The contact between the glucose polymers in accordance with the invention to be purified and the granular black carbon takes place in the countercurrent mode in the sense that the glucose polymer solution first of all comes into contact with the saturated granular black carbon at the bottom of the column.

The purified glucose polymers are therefore recovered at the top of the column of granular black carbon, at the place where the purified granular black carbon is added in the countercurrent mode.

In this way, the final layer of granular black carbon at the top of the column acts as a "safety barrier".

This arrangement can be controlled by carrying out granular black carbon "chase" operations. The column is stopped, the saturated granular black carbon is withdrawn by the bottom, and is replaced by the top with regenerated granular black carbon.

The saturated granular black carbon is desugared before being regenerated by heat treatment in a hearth furnace.

At start-up, and for safety, the first $m^3$ of branched soluble glucose polymers with a low dry matter content are downgraded.

The monitoring of the decrease in the level of contaminants (endotoxins, peptidoglycans and β-glucans) can be analyzed by taking a certain number of samples (five, for example) from the bottom of the column to the top;
  in a second variation of the process in accordance with the invention: in the case of the use of activated carbon, this configuration is based on a "double" treatment with activated carbon.

The branched soluble glucose polymers entering are mixed with activated carbon (between 0.5% and 5%, preferably between 0.5 and 1.5% relative to the dry matter to be treated) at a temperature of between 70 and 75° C. for one hour.

The glucose polymers are then filtered and analyzed.

The glucose polymers then undergo a treatment of the same nature. This second treatment is the "safety" treatment.

The applicant company recommends using activated carbon of different porosity in these two stages, so as to take into account the variability of the size of the contaminants;
  in a third variation of the process in accordance with the invention, it is chosen to combine a granular black carbon stage and an activated carbon stage.

The applicant company then recommends placing the column of granular black carbon at the head of this combination.

The conditions for implementing these two stages are in accordance with what is described hereinabove.

The second of the three means implemented for purifying the glucose polymers intended for the production of peritoneal dialysis solutions in accordance with the invention consists in using a sterilizing filtration.

This sterilizing filtration step consists principally of a membrane filtration where the pore diameter is 0.1 µm, preceded, where appropriate, by a membrane prefiltration where the pore diameter is 0.22 µm, itself preceded by a membrane filtration where the pore diameter is 0.45 µm.

This step makes it possible to retain any contamination by microorganisms, and in particular acidothermophilic bacteria of *Alicyclobacillus acidocaldarius* type, their size being greater than the filtration pore diameters.

The filtration is carried out using several cartridge filters inserted into a vertical casing toward which the syrup is directed.

These cartridge filters are supplied by the companies Pall or Millipore, for example. The size of the cartridges may be 10, 20 or 30 inches, and the number of cartridges installed makes it possible to obtain a filtration surface area sufficient to pass a product flow rate of between 1 and 20 l/minutes/m².

These cartridge filters have resistance capacities for continuous working at high temperature, of about 75° C., and for passing the abovementioned flow rate for a period of time greater than 700 h.

Working at a temperature above 75° C. makes it possible to limit any microbiological growth, in particular growth of thermophilic flora.

Their temperature resistance also makes it possible to carry out a sterilization before they are brought into service. This sterilization consists in passing steam at 2 bar through the casing for a period of 20 minutes. This sterilization is followed by rinsing with purified water (within the meaning of the Pharmacopeia) for a period of 5 minutes.

These filters also have capacities to withstand certain chemical products used for equipment cleaning operations, and in particular peracetic acid at a concentration of 5‰.

An integrity test can be carried out on these cartridges using an integrity test from the company Millipore for example. This integrity test is carried out when the cartridges are installed in order to verify the assembling thereof. This test is then carried out before each cleaning of the equipment and, finally, before the disassembling in order to validate the correct functioning of said cartridges during the production phase.

The working pressure difference ($\Delta P$) of these filters must not exceed 2 bar in order to guarantee their integrity. Should this be the case, these filters must be replaced with new ones.

A third and final means implemented for purifying the branched soluble glucose polymers intended for the production of peritoneal dialysis solutions in accordance with the invention can consist in using a particular heat treatment, which will be advantageously implemented at the end of these purification steps.

The applicant company has noted that this treatment is not essential for guaranteeing the high level of purification of the glucose polymers as provided by the process according to the invention, but can be implemented in the interests of safety.

More particularly, this heat treatment consists in regulating the time/temperature pair so as to eliminate the residual bioburden of thermophilic microorganisms capable of still contaminating said glucose polymers.

This heat treatment step then consists in heating at a temperature between 100 and 130° C., preferably at a temperature of 120° C., for 1 to 5 minutes, preferably 2 minutes.

This heat treatment is carried out by means of a tubular heat exchanger in which the glucose polymer solution circulates, said tubular heat exchanger being surrounded by a calender fed with steam at 2 bar in order to regulate therein a temperature of about 120° C.

This tubular heat exchanger, which is, for example, manufactured by the company Actini, consists of several parts:
- a section for recovery of energy produced/produced between the entry and the exit of the zone,
- a section for heating with steam at 2 bar,
- a holding section which is integrated and can be modulated according to the desired residence time.

The length of this heat exchanger is calculated in order to guarantee the desired residence time according to the feed flow rate. For example, the feed flow rate may be between 3000 and 4000 liters/hour for a holding section of about 100 to 130 liters.

In order to illustrate this purification treatment for the glucose polymers in accordance with the invention, one of the preferred processes consists, after the step of inactivation of the branching enzyme as specified at the end of step 2), or after the step of inhibiting the α-amylase as recommended at the end of the optional step 3), in carrying out the succession of the following steps:

i) bringing the pH of the aqueous solution containing the branched soluble glucose polymers to a value of between 4 and 5, preferably to a value of 4.5, ii) carrying out, on said resulting solution, two successive steps of treatment with activated carbon and/or with granular black carbon, iii) filtering on a filter with a pore diameter of 10 μm, and then on a filter with a pore diameter of 1 μm, iv) evaporating, concentrating and demineralizing the solution of branched soluble glucose polymers, v) carrying out a third step of treatment with activated carbon and/or with granular black carbon, vi) filtering on a filter with a pore diameter of 10 μm, and then on a filter with a pore diameter of 1.2 μm, vii) implementing a sterilizing filtration consisting of two membrane filtrations where the pore diameter is 0.45 μm then 0.22 μm.

The applicant company recommends, at the level of step 2), between the two successive treatments with activated carbon and/or with granular black carbon, getting rid of the particles and impurities of the solution resulting from the first treatment (for example, particles of contaminating carbon or granular black carbon), in order to avoid clogging of the columns of activated carbon and/or of granular black carbon that are subsequently used.

This removal of this mineral, or even organic, filler can be carried out under sterile conditions by any means known moreover to those skilled in the art.

It can be carried out, for example, using a sterile disk centrifuge separator, such as the one sold by the company Alfa Laval (BTUX type), using a microfiltration module such as the one sold by the company Pall and equipped with Membralox ceramic membranes, or using an Eaton bag filter with successive pore diameters of 50, 25 and 10 μm, as will be exemplified hereinafter.

This succession of steps thus makes it possible to increase, step by step, the safety of the production of the glucose polymers intended for the preparation of peritoneal dialysis solutions.

Entirely advantageously, these branched soluble glucose polymers, even in the presence of their coproducts, are entirely suitable for the peritoneal dialysis application for which they are intended.

Other features and advantages of the invention will become apparent on reading the nonlimiting examples described below.

EXAMPLE 1

Preparation of the Branched Soluble Glucose Polymers of the Invention by Means of Only the Branching Enzyme (First Family of Polymers in Accordance with the Invention)

A solution of starch containing 11% dry matter is prepared from a pea starch which is more than 95% rich in starch and has an amylose content of 36.7%.

For this, 110 g, dry, of pea starch are resuspended in 890 ml of water at ambient temperature and with stirring.

The pH is adjusted to 7.0 with 4% sodium hydroxide.

Total solubilization of the starch is carried out in a Jet Cooker at 150° C. for 4 minutes at a pressure of 4-5 bar, followed by atmospheric flash cooling to 70° C. by recirculation in a heat exchanger.

The glycogen-branching enzyme purified from *Bacillus stearothermophilus* is continuously added in a proportion of 3 ml of solution of enzyme at 45 000 U/ml per 100 g, dry, of substrate.

The enzymatic reaction is carried out for 15 hours at 70° C. and at pH 6.8, and then stopped by heating at 90° C. for 1 h.

The reaction medium is then brought back to a temperature of 70° C. and a pH of 4.5.

It is then treated on 1% d/d Norit SX+ activated carbon for 1 hour and filtered on Eaton bag filters with successive pore diameters of 50, 25 and 10 µm.

The resulting solution undergoes a further treatment with 1% by weight dry/dry (d/d) Norit SX+ activated carbon for 1 hour at 70° C., and then filtered on a Cricket filter having a pore size of 11 µm and then on a 1 µm Eaton filter.

The resulting product is concentrated to a dry matter content of about 30% on a Niro falling film evaporator.

Demineralization is carried out by passing over a mixed bed at a temperature of less than 40° C. and at a flow rate of 3 V/V/h.

The demineralized solution is heated to 70° C. and undergoes a third treatment with 1% d/d Norit SX+ activated carbon for 1 hour, and is then filtered on a Cricket filter with a pore diameter of 11 µm and then on Millipore cartridges with a pore diameter of 1.2 µm, followed by sterilizing filtration on a membrane with a pore diameter of 0.45 µm then 0.22 µm.

The solution is then spray-dried.

The glucose polymer thus purified has an endotoxin content <0.3 EU/g and a peptidoglycan content <20 ng/g and also an absence per g of aerobic microorganisms (yeasts, molds and thermophilic acidophilic bacteria).

The following table I presents the results of the physico-chemical characteristics of the branched soluble glucose polymer in accordance with the invention thus obtained, in comparison with icodextrin.

TABLE I

|  | Polymers in accordance with the invention | Icodextrin |
|---|---|---|
| α-1,6 linkage content | 8.7 | 8.4 | 7-7.5 |
| Mw (daltons) by light scattering (Da) | 127 000 | 144 000 | 22 000-21 500 |
| Reducing sugar content according to the test "B" (%) | 30 | 27 | 34-38 |
| Mw of the products released by GPC Nitrate (Da) | 10 375 | 9935 | 2700-3435 |
| Osmolality (mOsm/kg) | 13 | 13 | 10 |
| Chain length distribution | | | |
| DP < 10 | 30.1 | 36.0 | 21.9 |
| DP > 30 | 7.7 | 6.1 | 16.2 |
| Average DP | 11.4 | 10.7 | 12.7 |

The glucose polymers according to the invention exhibit notable glycemic and osmotic powers compared with those produced by icodextrin.

For an equivalent osmolality, the polymers according to the invention in fact express an amylase resistance that is greater than that of icodextrin.

It should be noted that the branched glucose polymers of the invention also differ from those prepared according to the teaching of patent EP 1 177 216, of which the applicant company is the proprietor.

This patent EP 1 177 216 taught the preferential treatment with the branching enzyme of a waxy (amylopectin-rich) starch derivative or starch, batchwise, and at 37° C.

The applicant company thus found that the glucose polymers obtained according to this patent EP 1 177 216 exhibit a less advantageous behavior with regard to the amylase resistance test, which is in particular reflected by released products having an Mw <6000 daltons, preferably between 5000 and 6000 daltons, i.e. half the size of the Mw values of the products released by the products produced according to this example 1.

These branched soluble glucose polymers therefore constitute the best compromise in terms of molecular weight, branched structure and behavior with regard to their amylase resistance, which marks them more particularly for use in peritoneal dialysis.

EXAMPLE 2

Preparation of the Branched Soluble Glucose Polymers of the Invention by Means of the Branching Enzyme Coupled with an α-amylase (Second Family of Polymers in Accordance with the Invention)

A solution of starch containing 11% dry matter is prepared from a pea starch which is more than 95% rich in starch and has an amylose content of 36.7%.

For this, 110 g, dry, of pea starch are resuspended in 890 ml of water at ambient temperature and with stirring.

The pH is adjusted to 7.0 with 4% sodium hydroxide.

Total solubilization of the starch is carried out in a Jet Cooker at 150° C. for 4 minutes at a pressure of 4-5 bar, followed by atmospheric flash cooling to 70° C. by recirculation in a heat exchanger.

The glycogen-branching enzyme purified from *Bacillus stearothermophilus* is continuously added in a proportion of 2 ml of solution of enzyme at 45 000 U/ml per 100 g, dry, of substrate.

The enzymatic reaction is carried out for 15 hours at 70° C. and at pH 6.8.

A supplementary treatment is carried out with α-amylase under the following conditions:

70 ppm dry/dry of calcium ions in the form of $CaCl_2$ are added.

The mixture is heated to 95° C.

0.15% V/dry of Termamyl® 120L at a concentration of 120 KNU/g is added.

The incubation is carried out for 45 minutes, and the reaction is stopped by lowering the pH to 3.5 with 10% HCl, and then the solution is maintained at pH 3.25 and at a temperature of 95° C. for 15 minutes.

The reaction medium is then brought back to a temperature of 70° C. and to a pH of 4.5, then treated on 1% d/d Norit SX+ activated carbon for 1 hour, and then filtered on Eaton bag filters with successive pore diameters of 50, 25 and 10 µm. The resulting solution undergoes a further treatment with 1% d/d Norit SX+ activated carbon for 1 hour at 70° C. and is then filtered on a Cricket filter with a pore size of 11 µm and then on a 1 µm Eaton filter.

The resulting product is concentrated to a dry matter content of about 30% on a Niro falling film evaporator.

Demineralization is carried out by passing over a mixed bed at a temperature of less than 40° C. and at a flow rate of 3 V/V/h.

The demineralized solution is heated to 70° C. and undergoes a third treatment with 1% d/d Norit SX+ activated carbon for 1 hour, and is then filtered on a Cricket filter with a pore diameter of 11 µm and then on Millipore cartridges with a pore diameter of 1.2 μm, followed by sterilizing filtration on a membrane with a pore diameter of 0.45 μm then 0.22 μm.

The solution is then spray-dried.

The glucose polymer thus purified has an endotoxin content <0.3 EU/g and a peptidoglycan content <20 ng/g, and also an absence per g of aerobic microorganisms, yeasts, molds and thermophilic acidophilic bacteria.

The following table II presents the results of the physicochemical characteristics of the branched soluble glucose polymer in accordance with the invention thus obtained, in comparison with icodextrin.

TABLE II

|  | Polymer in accordance with the invention | Icodextrin |
|---|---|---|
| α-1,6 linkage content | 8.7 | 8.8 | 7-7.5 |
| Mw (daltons) by light scattering (Da) | 58 400 | 55 000 | 22 000-21 500 |
| Reducing sugar content according to the test "B" (%) | 33 | 32 | 34-38 |
| Mw of the products released by GPC Nitrate (Da) | 6660 | 6970 | 2700-3435 |
| Osmolality (mOsm/kg) | 65 | 87 | 10 |
| Chain length distribution |  |  |  |
| DP < 10 | 72.2 | 75.6 | 21.9 |
| DP > 30 | 2.8 | 2.5 | 16.2 |
| Average DP | 5.1 | 4.7 | 12.7 |

The glucose polymers obtained by means of this variation of the process according to the invention themselves also exhibit an entirely notable behavior from the viewpoint of the α-amylase resistance test and in particular with regard to the Mw of the products released.

The invention claimed is:

1. Branched soluble glucose polymers prepared from starch having an amylose content of between 35 and 80% by weight, having an α-1,6 glucosidic linkage content of between 8 and 9%, and an Mw of between 50 000 and 150 000 daltons, wherein the polymers exhibit a resistance to pancreatic alpha-amylase expressed via:
   a reducing sugar content of between 25 and 35%, and
   an Mw of the released products of between 6000 and 12 000 daltons, and
   wherein the polymers have a branched-chain-length distribution profile consisting of:
   25 to 80% of DP<10,
   2 to 10% of DP>30,
with an average DP of between 4 and 12.

2. The polymers as claimed in claim 1, wherein the polymers have an osmolality, determined according to a test A, with a value of less than 100 mOsm/kg, the test A consisting in determining the osmolality of a solution containing 100 g, dry, of said branched glucose polymers placed in 1 kg of water, using a Mark 3 osmometer from Fiske® Associates.

3. The polymers as claimed in claim 1, wherein the polymers exhibit a resistance to pancreatic alpha-amylase expressed via:
   a reducing sugar content of greater than or equal to 25% and less than 30%,
   an Mw of the released products of greater than or equal to 9500 and less than 12 000 daltons.

4. The polymers as claimed in claim 3, wherein the polymers have an osmolality, determined according to a test "A", with a value of between 10 and 20mOsm/kg.

5. The polymers as claimed in claim 3, wherein the polymers have a branched-chain-length distribution profile consisting of:
   25 to 40% of DP <10,
   5 to 10% of DP >30,
   with an average DP of between 10 and 12.

6. The polymers as claimed in claim 1, wherein the polymers exhibit a resistance to pancreatic alpha-amylase expressed via:
   a reducing sugar content of greater than or equal to 30% and less than 35%,
   an Mw of the released products of greater than or equal to 6000 daltons and less than 9500 daltons.

7. The polymers as claimed in claim 6, wherein the polymers have an osmolality, determined according to a test "A", with a value of between 50 and 100mOsm/kg.

8. The polymers as claimed in claim 6, wherein the polymers have a branched-chain-length distribution profile consisting of:
   65 to 80% of DP <10,
   2 to 5% of DP >30,
   with an average DP of between 4 and 6.

9. A process for preparing the branched soluble glucose polymers as claimed in claim 1, comprising the succession of following steps:
   1) bursting and solubilization of a milk of starch having an amylose content of at least 30% by weight, preferably between 35 and 80% by weight, and a dry matter content of between 5 and 25%,
   2) continuous addition of a glycogen-branching enzyme extracted from thermophilic microorganisms, having an activity of between 25 000 U/ml and 60 000 U/ml, at a dose of between 800 and 2500 U/g, dry, of starch, at a temperature of between 60° C. and 80° C., for a period of from 12 to 18 hours,
   3) optionally, treatment with a starch-liquefying enzyme of α-amylase type having an activity of between 100 and 150 KNU/ml at a temperature of 95° C., a pH of between 5 and 8, for 30 to 60minutes,
   4) purification of the resulting branched soluble glucose polymers by means of:
      at least one step of treatment with activated carbon and/or with granular black carbon,
      at least one sterilizing filtration step, and optionally, at least one heat treatment step,
   5) recovery of the resulting purified branched soluble glucose polymers.

10. The process as claimed in claim 9, wherein the purification step 4) comprises the succession of following steps:
   i) bringing the pH of the aqueous solution containing the branched soluble glucose polymers to a value of between 4 and 5,
   ii) carrying out, on said resulting solution, two successive steps of treatment with activated carbon and/or with granular black carbon,
   iii) filtering on a filter with a pore diameter of 10 μm, and then on a filter with a pore diameter of 1 μm,
   iv) evaporating, concentrating and demineralizing the solution of branched soluble glucose polymers,
   v) carrying out a third step of treatment with activated carbon and/or with granular black carbon,
   vi) filtering on a filter with a pore diameter of 10 μm, and then on a filter with a pore diameter of 1.2 μm,
   vii) implementing a sterilizing filtration consisting of two membrane filtrations where the pore diameter is 0.45 μm then 0.22 μm.

11. The polymers as claimed in claim 4, wherein the polymers have a branched-chain-length distribution profile consisting of:
   25 to 40% of DP <10,
   5 to 10% of DP >30,
   with an average DP of between 10 and 12.

12. The polymers as claimed in claim 7, wherein the polymers have a branched-chain-length distribution profile consisting of:
   65 to 80% of DP <10,
   2 to 5% of DP >30,
   with an average DP of between 4 and 6.

* * * * *